United States Patent [19]

Hattori et al.

[11] Patent Number: 5,334,713
[45] Date of Patent: Aug. 2, 1994

[54] N-LONG CHAIN ACYL NEUTRAL AMINO ACID ESTERS

[75] Inventors: Tatsuya Hattori; Naoko Mikami, both of Kawasaki, Japan

[73] Assignee: Ajinomoto Co., Inc., Tokyo, Japan

[21] Appl. No.: 964,310

[22] Filed: Oct. 21, 1992

[30] Foreign Application Priority Data

Oct. 21, 1991 [JP] Japan .................... 3-272455

[51] Int. Cl.$^5$ .................. C07J 41/00; C07J 43/00
[52] U.S. Cl. .................. 540/113; 552/544
[58] Field of Search .................. 552/544; 540/113

[56] References Cited

U.S. PATENT DOCUMENTS

| | | | |
|---|---|---|---|
| 3,968,105 | 7/1976 | Gray | 260/239.5 |
| 4,614,619 | 9/1986 | Shannon | 260/397.2 |
| 5,153,340 | 10/1992 | Ichikawa et al. | 552/509 |

FOREIGN PATENT DOCUMENTS 0443592  8/1991  European Pat. Off. .

OTHER PUBLICATIONS

Chemical Abstracts, AN 178666e, vol. 103, No. 22, Dec. 2, 1985, G. Quentin, et al., "Polymer Support Of A Steroid with a Peptide Spacer".

Chemical Abstracts, AN 861119w, vol. 94, No. 12, Mar. 23, 1981, "Emulsifier Composition", p. 118.

*Primary Examiner*—James H. Reamer
*Assistant Examiner*—Kimberly J. Kestler
*Attorney, Agent, or Firm*—Oblon, Spivak, McClelland, Maier & Neustadt

[57] ABSTRACT

The present invention relates to N-long chain acyl neutral amino acid esters of the general formula (I):

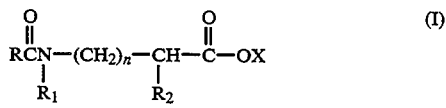

wherein X represents an ester-forming residue of a sterol; COR represents a long chain acyl group having 8 to 22 carbon atoms; $R_1$ and $R_2$ are identical or different from each other, each represents a hydrogen atom or a straight chain or branched alkyl group having 1 to 4 carbon atoms, or $R_1$ and $R_2$ together form an alkylene group; and n represents 0, 1 or 2. The compounds are particularly useful in cosmetic or pharmaceutical preparations for external use.

4 Claims, No Drawings

N-LONG CHAIN ACYL NEUTRAL AMINO ACID ESTERS

BACKGROUND OF THE INVENTION

1. Field of the Invention:

The present invention relates to N-long chain acyl neutral amino acid esters comprising an ester forming residue of a sterol esterified with the carboxy group of a neutral amino acid, and to a cosmetic or a pharmaceutical preparation for external use each containing such ester(s).

Various kinds of esters have generally been used as materials for the oil-phase in skin and hair cosmetics and in medicines for external application. Further, amino acid type surface active agents of natural origin which are very safe have been used recently. Most of such amino acid type surface active agents are hydrophilic. As oil-soluble amino acid type surface active agents, usable as oil-phase materials for cosmetics and pharmaceuticals, N-lower acyl acidic amino acid diesters, N-long chain acyl neutral amino acid and N, N-di-long chain acyl basic amino acid esters are known.

However, although the known compounds as described above have some degree of emulsifying and hydrating performances, the emulsifying and hydrating actions of N-long chain acyl acidic amino acid higher alcohol diesters are remarkably low. For the improvement of the performance, for example in cosmetics, greater effectiveness is required.

On the other hand, various kinds of sterol esters have hitherto been used as an oil-phase material having excellent emulsifying performance. They have particularly preferred hydrating performance but involve the drawback that the use of cosmetics to which they are blended results in a somewhat heavy feeling.

The problem underlying the present invention is to provide novel ester compounds of oil-soluble N-long chain acyl neutral amino acids which have excellent emulsifying capacity and further to provide cosmetic and external pharmaceutical preparations comprising these novel ester compounds, which have excellent moisturizing action and do not a heavy feeling on the skin.

SUMMARY OF THE INVENTION

The present invention relates to N-long chain acyl neutral amino acid esters of the general formula (I)

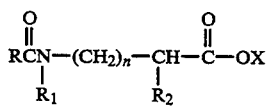

wherein X represents an ester-forming residue of a sterol; COR represents a long chain acyl group having 8 to 22 carbon atoms; $R_1$ and $R_2$ are identical or different from each other, and each represents a hydrogen atom or a straight chain or branched alkyl group having 1 to 4 carbon atoms, or $R_1$ and $R_2$ together form an alkylene group; and n represents 0, 1 or 2.

Subject matter of the present invention also includes cosmetic and pharmaceutical preparations for external topical use containing at least one N-long chain acyl neutral amino acid ester according to formula (I).

The amino acid part in the N-long chain acyl neutral amino acid moiety of the ester of formula (I) may be derived from any neutral amino acid, particularly a natural amino acid. Examples thereof include glycine, alanine, aminobutyric acid, valise, norvaline, leucine, isoleucine, norleucine, alloisoleucine, proline, etc. The neutral amino acid moiety may be in an optically active form or the racemic form. The long chain acyl group in the moiety is an acyl group derived from a straight chain or branched saturated or unsaturated fatty acid with 8 to 22 carbon atoms, including, for example, acyl groups of single fatty acids such as lauric acid, palmitic acid, stearic acid and oleic acid, as well as acyl groups of natural fatty acid mixtures (including branched fatty acids) such as coconut oil fatty acids, tallow fatty acids.

Such long chain acyl groups provide hydrophobicity to the ester.

As sterols in the ester, there can be mentioned, for example, cholesterol, phytosterol and hydrogenated products of them (which may be of animal or vegetable origin).

The ester represented by general formula (I) of the present invention can be prepared by reacting an N-long chain acyl neutral amino acid and a sterol by generally known esterification methods, for example (1) thermal dehydrating condensation reaction (under normal pressure or reduced pressure), (2) ester-exchange reaction and (3) azeotropic dehydrating condensation reaction. Of these, the azeotropic dehydrating condensation reaction is the most preferred one, in view of the reaction conditions and the yield and purity of the product.

According to an example of the esterification method one mole of an N-long chain acyl neutral amino acid and from 1.0 to 1.2 moles of a sterol are dissolved in a non-polar solvent such as benzene or toluene and stirred. Then 0.01 to 1.5 moles of an acidic catalyst such as sulfuric acid, p-toluenesulfonic acid, hydrogen chloride or a strong acidic ion-exchange resin is added thereto and heated with stirring at 70° to 200° C. for 1 to 10 hours. During the reaction, water produced as a by-product is removed as much as possible to accelerate the reaction.

The preparation method is of course not restricted to the above-mentioned methods but any method may be used as long as the N-long chain acyl neutral amino acid ester is finally produced. For example, a method of reacting at first a neutral amino acid with a sterol in the presence of an acidic catalyst to form the corresponding neutral amino acid ester, which is then acylated to the N-long chain acyl derivative by Schotten-Baumann reaction in which the ester is reacted with a long chain fatty acid halide in the presence of a basic catalyst.

The N-long chain acyl neutral amino acid esters of the present invention have improved properties compared with known N-acyl amino acid esters. They are free from the drawback of the low emulsifying capacity of conventional higher alcohol diesters of N-long chain acyl amino acids, due to the presence of a sterol residue in the ester portion. By adding the N-long chain acyl neutral amino acid ester of the present invention to other oil bases, the hydrating capacity of the resulting compositions may be elevated and the compositions may further be provided with a gelling capacity. In addition, the mixed compositions may thereby be provided with thixotropic properties. Since the ester of the present invention has an amino acid moiety, the ester is characterized by having an affinity to the skin and hair and having an emollient capacity towards them.

The invention is further directed to a cosmetic or pharmaceutical preparation for external use containing the above described compound(s) of the invention.

When the compound of the present invention is incorporated into a cosmetic or a pharmaceutical external preparation, it may be a substitute for an oily base, for example animal and vegetable oils, such as squalene, castor oil, bees wax, lanolin, jojoba oil, carnauba wax, tung oil, sesame oil, evening primrose oil, palm oil or mink oil, mineral oils such as solid paraffin, silicone oil, ceresine, liquid paraffin or vaseline, synthetic oils such as isopropyl myristate or synthetic polyethers, as well as emollients such as cholesteryl stearate or cholesteryl hydroxystearate, or may be used in combination with any of such oily bases.

The present inventors have found that when the ester of the present invention is incorporated into skin cosmetics such as face wash cream, face wash foam, cleansing cream, massage cream, cold cream, moisture cream, emulsions, lotions, packings, or baby skin protectors, it shows an extremely excellent performance as an oily base and also as an emulsifier and imparts an excellent affinity to the skin to emulsified products, since it contains a sterol ester moiety, being different from conventional higher alcohol diesters of N-long chain acyl amino acids. In addition, it has also been found that (a) when the ester of the present invention is incorporated into emulsified products, the resulting products have an extremely smooth feeling to the skin and also have thixotropic properties. These advantageous effects could not be expected, since when conventional sterol esters are incorporated into emulsified products, the touch of the resulting products to the skin in use becomes heavy; (b) in particular, when the ester of the present invention is incorporated into basic cosmetics, makeup cosmetics and suntan cosmetics such as foundation cream, foundation emulsion, face powder, lipstick, lip cream, cheek rouge, eye makeup, eyebrow pencil, eyelash cosmetics and nail cosmetics, as well as into perfumes and Eau de Cologne, the cosmetic products obtained have good dispersibility of pigments therein, are well-spreadable, water-repellent and resistant to sweat; (c) when the ester of the present invention is incorporated into hair-care products such as hair cream, perfumed hair oil, hair liquid, brilliantine, hair cream stick, liquid hair conditioner, set lotion, treatment, hair tonic, hair spray and hair color, the products give softness and gloss to the hair treated therewith; (d) when the ester of the present invention is incorporated into aerosol products, it is well-compatible with the propellant, such as LPG, to give one-component aerosol products; and (e) when the ester of the present invention is incorporated into shampoo, hair rinse, soap, bath cosmetics and shaving cosmetics, the resulting shampoo and hair rinse have a strong affinity to the hair and hence have a good conditioning effect towards the hair treated therewith, and further show a moisturizing effect. Since the ester is an amino acid derivative, the resulting soaps, bath cosmetics and shaving cosmetics have a skin chapping preventing effect to the skin as treated therewith since they leave suitable oil components to the skin after use.

When the compound of the present invention is used as an oily material of a pharmaceutical preparation for external use, the feeling on the skin of a patient is excellent since it has an excellent affinity to the skin and may promote the absorption of the drug components in the skin and it is not sticky to the skin. In addition, it is able to impart a thixotropic property to non-thixotropic conventional oily preparations and external drugs, hence the ester of the present invention has been found to be applicable to various uses of a broad field, such as for lotions, aerosols, jellies, liniments, ointments and pastes.

The cosmetic or external pharmaceutical preparation of the present invention may further contain surfactant(s), which is/are selected from anionic surfactants such as N-long chain fatty acid acylglutamic acid salts, N-long chain fatty acylsarcosine salts, N-long chain fatty acid-N-methyltaurin salts, N-acyl-N-methyl-$\beta$-alaninate alkyl sulfates, alkylbenzenesulfonates, alkyloxysulfonates, fatty acid amide ether sulfates, fatty acid salts, higher alcohol ester salts of sulfosuccinic acid, polyoxyethylene alkylsulfates, fatty acid ester salts of isethionic acid, alkyl ether carboxylic acid salts, etc.; nonionic surfactants such as glycerin ethers, polyoxyethylene ethers thereof and the like, ether nonionic surfactants, polyoxyethylene ethers of glycerin esters, polyoxyethylene ethers of sorbitan esters and the like, nonionic ether ester surfactants, polyoxyethylene fatty acid esters, glycerin esters, sorbitan esters, fatty acid esters of sucrose and the like, nonionic ester surfactants, fatty acid alkanol amides, and polyoxyethylene fatty acid amides and the like, nonionic nitrogen-containing surfactants, etc.; cationic surfactants such as alkylammonium chlorides, dialkylammonium chlorides and the like, aliphatic amines and quaternary ammonium salts thereof, benzalkonium salts and the like, aromatic quaternary ammonium salts, and acyl arginine esters of fatty acids, etc.; as well as ampholytic surfactants such as carboxybetain and the like, ampholytic betaine surfactants, aminocarboxylic acids, imidazoline derivatives, etc.; and mixtures of them.

As the aqueous phase ingredient to be used in the cosmetic and external pharmaceutical preparation of the present invention, there are mentioned, for example, polyalcohols such as glycerin, ethylene glycol, 1,3-butylene glycol, etc.; water-soluble polymers such as polyethylene glycol, alginic acid salts, carboxymethyl cellulose, hyaluronic acid, water-soluble chitin, sodium polyglutaminate, etc.; glycoalcohols such as sorbitol, mannitol, etc., and ethylene oxide or propylene oxide adducts of them; organic acids such as citric acid, succinic acid, lactic acid, PCA, etc., and their salts; as well as lower alcohols such as ethanol, propanol, etc.

As the powdery ingredient to be used in the cosmetic compositions of the present invention, there are mentioned, for example, inorganic powders such as talc, kaolin, titanium dioxide, mica, sericite, etc.; as well as organic powders such as N-mono-long chain acyl basic amino acids, guanine, polymer resins, laminate resin pearls, etc.

The cosmetics of the present invention may further contain ordinary cosmetic aids, such as whitening agents, thickeners, softeners, moisturizers, superratting agents, emollients, wetting agents, preservatives, UV absorbents, drugs, defoaming agents, chelating agents, protective colloids, perfumes, colorants, as well as other desired components generally incorporated into cosmetics.

As the drug component useful to be incorporated into the external pharmaceutical preparation of the present invention, mentioned is any pharmaceutical agent useful in a pharmaceutical composition for the external application. It includes, for example, antioxidants, antiseptics, antipyretics, sedatives, disinfectants, bactericides, fungicides, keratin softening and peeling agents, skin bleaching agents, skin coloring agents, granulation and epidermization promoters, necrotic tissue removing agents, hair-growing agents, epilatories, suntan agents, antiperspirants, deodorants, hormones, vitamins, etc.

The amount of the ester of the present invention to be added to the cosmetic and external pharmaceutical preparation is chosen to make sure that the ester added may well display the described ester effects of the present invention in the cosmetic and external pharmaceutical preparation, which may easily be determined by anyone skilled in the art.

DESCRIPTION OF THE PREFERRED EMBODIMENTS

The present invention will be explained further by means of production examples and application examples (and examples for the production of cosmetic and external pharmaceutical preparations) which are provided herein for purposes of illustration only and are not intended to be limiting unless otherwise specified.

PREPARATION EXAMPLE 1

Preparation of N-lauryl-L-sarcosine cholesterol ester 190 g (0.7 mol) of N-lauroyl-L-sarcosine and 284 g (0.74 mol) of cholesterol were dissolved in 300 ml of toluene. Then, 0.5 ml of sulfuric acid was added as a catalyst, and the mixture was heated to 130°–140° C. for about 4 hours. After repeated washing with water, toluene was removed by distillation and 410 g of white powdery compound (A) was obtained. The compound had an acid value of 0.4 and a saponification value of 83.

PREPARATION EXAMPLE 2

Preparation of N-lauroyl-L-leucine cholesterol ester

The same process as in Production Example 1 was repeated, except that 209 g of N-lauroyl-L-leucine was used in place of N-lauroyl-L-sarcosine in the esterification, to obtain 420 g of white powdery compound (B). The compound had an acid value of 0.2 and a saponification value of 80.

PREPARATION EXAMPLE 3

Preparation of N-palmitoyl-L-proline cholesterol ester

The same process as in Production Example 1 was repeated, except that 247 g of N-palmitoyl-L-proline was used in place of N-lauroyl-L-sarcosine in the esterification, to obtain 460 g of white solid compound (C). The compound had an acid value of 1.0 and a saponification value of 72.

PREPARATION EXAMPLE 4

Preparation of N-lauroyl-N-methyl-B-alanine cholesterol ester

The same process as in Production Example 1 was repeated, except that 209 g of N-lauroyl-N-methyl-$\beta$-alanine was used in place of N-lauroyl-L-sarcosine in the esterification, to obtain 435 g of white solid compound (D). The compound had an acid value of 0.8 and a saponification value of 78.

Application examples are mentioned below, in which the proportion of the components is represented by % by weight. Compounds according to formula (I) are referred to by the letters given in the aforementioned preparation examples.

APPLICATION EXAMPLE 1

O/W (oil-in-water) Cream

Components (1) shown in Table 1 below were heated up to 80° C., and components (2) therein up to 70° C. With stirring components (1), components (2) were gradually added thereto and emulsified. With cooling in a water bath and with stirring, component (3) was added to the resulting emulsion at 50° C. and cooled to 35° C. to obtain a O/W cream as the product. The antiseptic, as mentioned previously, may be anyone of those ordinarily used in a pharmaceutical composition for external application and is easily selected by the skilled artisan. In this example the antiseptic is methylparaben (methyl p-hydroxybenzoate).

TABLE 1

| | Composition | Proportion (%) |
|---|---|---|
| Components 1 | Squalana | 15.0 |
| | Ester (A) of the invention | 5.0 |
| | Cetyloctanoate | 10.0 |
| | Hardened Oil | 5.0 |
| | Cetanol | 2.0 |
| | Self-emulsifying Glycerin Monostearate | 4.0 |
| | Diglycerin Oleate | 1.0 |
| | Dimethlpolysiloxane | 0.3 |
| Component 2 | Sodium N-stearoyl-L-glutaminate | 0.4 |
| | Xanthane Gum | 0.05 |
| | 1,3-Butylene Glycol | 7.0 |
| | Antiseptic (methylparaben) | 0.2 |
| | Pure Water | 47.85 |
| Component 3 | Perfume | 0.2 |
| | Total | 100.0 |

A glossy and well emulsified O/W cream (X) containing the ester (A) of the present invention was obtained, which had an excellent emollient property and gave a good feeling to users.

COMPARATIVE EXAMPLE 1

Next, for comparison, O/W cream sample (Y) was prepared, which comprised the same components mentioned above but contained dioctyldodecyl N-lauroyl-L-glutaminate in place of the ester (A) of the present invention. The two samples were applied to 18 to 25-years old adult panelists (20 men, 20 women) for a blind sensual test. The test results are shown in Table 2 below.

TABLE 2

| Test Sample | Spreadability | | Emollient Property | | Feeling in Use | |
|---|---|---|---|---|---|---|
| | men | women | men | women | men | women |
| X | 16 | 18 | 17 | 20 | 17 | 19 |
| Y | 4 | 2 | 3 | 0 | 3 | 1 |

The numerals in Table 2 indicate the numbers of panelists who judged that the test sample was good.

The cream sample containing the ester of the present invention showed better results than the comparative sample in all the tested items. As is noted from the test results above, the ester of the present invention improved the spreadability, emollient property and feeling in use of the cream.

APPLICATION EXAMPLE 2

Milky Lotion

Components (1) shown in Table 3 below were heated up to 85° C. and components (2) were heated up to 70° C. With stirring components (2), components (1) were gradually added thereto and cooled to 30° C. with stirring to obtain a milky lotion sample. The antiseptic used in this example is the same as that used in Application Example 1.

TABLE 3

|  | Composition | Proportion (%) |
|---|---|---|
| Components 1 | Squalene | 10.0 |
|  | Ester (D) of the invention | 2.0 |
|  | Isocetyl Octanoate | 10.0 |
|  | Glycerin Trioctanoate | 4.0 |
|  | Propylene Glycol Stearate | 0.5 |
|  | Behenyl Alcohol | 0.5 |
|  | Stearic Acid | 1.0 |
|  | Oleophilic Glycerin Monostearate | 1.0 |
|  | Diglycerin Oleate | 0.5 |
|  | Polyethylene Glycol Stearate | 2.5 |
| Components 2 | Water-soluble Chitin (1% aqueous solution) | 15.0 |
|  | Oleyl Phosphate | 0.4 |
|  | 1,3-Butylene Glycol | 5.0 |
|  | Antiseptic (methylparaben) | 0.2 |
|  | Pure Water | 47.4 |
|  | Total | 100.0 |

A stable emulsion having finely emulsified droplets incorporating the ester (D) of the present invention was obtained, and the milky lotion containing it had improved skin affinity and adhesiveness and gave a good feeling to the skin in use.

APPLICATION EXAMPLE 3

Powdery Foundation

Components (1) shown in Table 4 below were blended and ground with a grinder. The ground powder was transferred to a high speed blender, and components (2) and then pigments were added thereto and uniformly blended. The blend was treated with a grinder and sieved to unify the grains, which were then shaped under compression to obtain a powdery foundation. The identity and quantity of the antiseptic and perfume can be easily selected according to the desires of the skilled artisan; in this example the antiseptic is butylparaben (butyl p-hydroxybenzoate) used in 0.2% and the perfume was used in 0.1%.

TABLE 4

|  | Composition | Proportion (%) |
|---|---|---|
| Components 1 | Red Iron Oxide | 3.0 |
|  | Yellow Iron Oxide | 2.5 |
|  | Black Iron Oxide | 0.5 |
|  | Nylon Powder | 10.0 |
|  | Titanium Oxide | 10.0 |
|  | Mica | 20.0 |
|  | Talc | 44.0 |
| Component 2 | Liquid Paraffin | 4.7 |
|  | Octyldodecyl Myristate | 2.5 |
|  | Ester (B) of the Invention | 2.5 |
|  | Antiseptic (butylparaben) | 0.2 |
|  | Perfume | 0.1 |
|  | Total | 100.0 |

The powdery foundation thus obtained was easily applied to the skin and had excellent spreadability.

APPLICATION EXAMPLE 4

Lipstick

Components (1) shown in Table 5 below were uniformly melted under heat at 80° C. To this were added components (2) in the same. The mix was kneaded and uniformly dispersed with a roll mill. After again melted, components (3) were added, defoamed, cast into a mold and rapidly cooled to obtain lipsticks. As before, the identity and quantity of components (3) can be easily selected according to the desires of the skilled artisan. In this example the antiseptic is butylparaben (butyl p-hydroxybenzoate) used in 0.2%, the antioxidant was vitamin E, used in 0.01%, and the perfume was used in 0.1%.

TABLE 5

|  | Composition | Proportion (%) |
|---|---|---|
| Components 1 | Castor Oil | 51.9 |
|  | Octyldodecanol | 10.0 |
|  | Ester (C) of the Invention | 10.0 |
|  | Liquid Lanolin | 5.0 |
|  | Bees Wax | 5.0 |
|  | Ozocerite | 4.0 |
|  | Candellila Wax | 7.0 |
|  | Carnauba Wax | 2.0 |
| Components 2 | Titanium Dioxide | 1.0 |
|  | Red No. 201 | 1.0 |
|  | Red No. 202 | 2.0 |
|  | Yellow No. 4 Aluminum Chelate | 1.0 |
|  | Red No. 223 | 0.1 |
| Components (3) | Perfume | 0.1 |
|  | Antioxidant (vitamin E) | 0.01 |
|  | Antiseptic (butylparaben) | 0.2 |
|  | Total | 100.0 |

The lipsticks obtained were stable for a long period of time without sweating. They had a suitable strength and had a good affinity to the skin and an excellent spreadability.

APPLICATION EXAMPLE 5

O/W Emulsion Ointment

Components (1) shown in Table 6 below were melted under heat at 75° C., and components (2) therein as melted under heating at 75° C. were added thereto. After stirred until the blend was solidified, an O/W emulsion base was obtained. Next, a small amount of the base was kneaded with a powder of adrenocortical hormone, and the remaining base was gradually added thereto and well kneaded to obtain a homogeneous O/W emulsion ointment.

TABLE 6

|  | Composition | Proportion (%) |
|---|---|---|
| Components 1 | White Vaseline | 25.0 |
|  | Stearyl Alcohol | 20.0 |
|  | Ester (D) of the Invention | 5.0 |
| Components 2 | Propylene Glycol | 12.0 |
|  | Sodium Laurylsulfate | 1.0 |
|  | Ethyl Parahydroxybenzoate | 0.03 |
|  | Propyl Parahydroxybenzoate | 0.02 |
|  | Pure Water | 36.95 |
|  | Total | 100.0 |

TABLE 7

| Composition | Proportion (g) |
|---|---|
| adrenocortical hormone | ad lib. |
| O/W Emulsion Base | 100 as a whole |

The ointment thus obtained had good spreadability and affinity to the skin and was not sticky to the skin.

ADVANTAGE OF THE INVENTION

The esters of the present invention have an excellent emulsifying property. When combined with other oily materials the esters of the present invention may enhance the hydrating capacity of the materials and may well gel the same. In addition, they give a good feeling in use and have good affinity to the hair and skin.

Having now fully described the invention, it will be apparent to one of ordinary skill in the art that many changes and modifications can be made thereto without departing from the spirit or scope of The invention as set forth herein.

We claim:

1. N-long chain acyl neutral amino acid esters of the general formula (I):

wherein X represents an ester-forming residue of a sterol; COR represents a long chain acyl group having 8 to 22 carbon atoms; $R_1$ and $R_2$ are identical or different from each other, and each represents a hydrogen atom or a straight chain or branched alkyl group having 1 to 4 carbon atoms, or $R_1$ and $R_2$ together form an alkylene group; and n represents 0, 1 or 2.

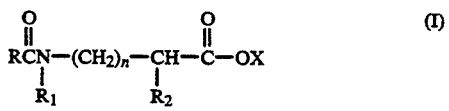

2. The compound of formula (I) as in claim 1 wherein the long chain acyl group is selected from the group consisting of lauric acid, palmitic acid, stearic acid, oleic acid, coconut oil fatty acids and tallow fatty acids.

3. The compound of formula (I) as in claim 1 wherein the sterol is selected from the group consisting of cholesterol, phytosterol, and hydrogenated products thereof.

4. The compound of formula (I) as in claim 1 wherein the long chain acyl group is palmitic acid and the sterol group is cholesterol.

* * * * *